United States Patent [19]

Danehy

[11] 4,259,443

[45] Mar. 31, 1981

[54] SYNTHESIS OF ASCORBIC ACID FROM LACTOSE

[75] Inventor: James P. Danehy, South Bend, Ind.

[73] Assignee: Bernard Wolnak and Associates, Inc., Chicago, Ill.

[21] Appl. No.: 47,937

[22] Filed: Jun. 12, 1979

Related U.S. Application Data

[63] Continuation-in-part of Ser. No. 9,251, Feb. 5, 1979, abandoned.

[51] Int. Cl.³ .......................... C12N 9/04; C12P 7/58; C12P 7/60
[52] U.S. Cl. .................................. 435/137; 435/138; 435/190
[58] Field of Search .............. 435/137, 138, 146, 155, 435/190; 260/343.7; 195/31 R, 32

[56] References Cited

U.S. PATENT DOCUMENTS

| | | | |
|---|---|---|---|
| 2,265,121 | 12/1941 | Reichstein | 260/340.7 |
| 2,462,251 | 2/1949 | Bassford et al. | 260/340.7 |
| 2,606,186 | 8/1952 | Dean et al. | 536/4 |
| 2,681,858 | 6/1954 | Stimpson | 426/580 X |
| 2,917,435 | 12/1959 | Perlman | 435/138 |
| 4,048,018 | 9/1977 | Coughlin et al. | 435/137 X |

FOREIGN PATENT DOCUMENTS

763055 12/1956 United Kingdom .

OTHER PUBLICATIONS

Cadotte et al., *J. Amer. Chem. Soc.*, 74, 1501, (1952).

*Primary Examiner*—Esther M. Kepplinger
*Attorney, Agent, or Firm*—Eugene F. Friedman

[57] ABSTRACT

A method of synthesizing vitamin C (ascorbic acid) directly from the hydrolysis products of lactose. Lactose, economically obtained from whey, undergoes hydrolysis with a warm aqueous slurry of lactase to produce D-galactose and D-glucose. Preparing the methyl glycosides of these two sugars protects a labile C-O linkage during the oxidation of the sugars to D-galacturonic acid and D-glucuronic acid. The mixture of these acids, after the removal of the methyl group through hydrolysis, undergoes reduction with gaseous hydrogen in the presence of an Adams catalyst or Raney nickel to produce a mixture of L-gulonic acid and L-galactonic acid. Removing the water from these acids forces their conversion into the corresponding lactones. Because of the applicable rate constants, adding water to the lactones does not result in their rapid reconversion to the acids. Accordingly, they can then undergo oxidation, in the presence of an enzyme obtained from pea seeds, to L-ascorbic acid.

15 Claims, No Drawings

SYNTHESIS OF ASCORBIC ACID FROM LACTOSE

CROSS REFERENCE TO RELATED APPLICATION

This application is a continuation-in-part of U.S. patent application Ser. No. 9,251, filed Feb. 5, 1979, and now abandoned.

BACKGROUND

Ascorbic acid (vitamin C) represents an essential nutrient of a proper diet for human beings. To assure the ingestion of this vitamin in sufficient quantities, many individuals regularly supplement their diets with doses of pure vitamin C.

To supply the demand for the vitamin, different processes have proven successful in synthesizing it from other ingredients. Presently, the method disclosed by T. Reichstein, in his U.S. Pat. No. 2,265,121, finds commercial use. That process, however, has only shown itself effective on a starting material of D-glucose or its precursor, corn syrup. A critical stage in the process involves the conversion of 2-keto-L-gulonic acid or derivatives yielding that acid to ascorbic acid. The 2-keto-L-gulonic acid, when treated with acid and warmed to at least 60° C., converts to the ascorbic acid.

However, glucose, the starting material for the Reichstein synthesis represents a generally useful commodity with a market price. Its cost forms a portion of the ultimate charge to the customer.

F. A. Isherwood et al., in their British Pat. No. 763,055, show that γ-lactones of L-gulonic acid or L-galactonic acid may be enzymatically oxidized to ascorbic acid. A group of enzymes which catalyze this reaction appear in seed, animal tissues and many microorganisms. However, the process of Isherwood et al. does not show how to reduce the cost of the initial reactants used to produce the vitamin.

Van Eekelen et al., in U.S. Pat. No. 2,491,065, convert 2-keto-L-gulonic acid to ascorbic acid by heating it in pure water at above 130° C. Bassford, Jr., et al., in their U.S. Pat. No. 2,462,251, use an organic solvent during the rearrangement of the keto-gulonic acid to ascorbic acid. The solvent should lack the ability to form a miscible solution with hydrochloric acid or to dissolve the ascorbic acid. The rearrangement to ascorbic acid takes place under heated conditions with hydrochloric acid which then distills off as an azeotropic mixture with part of the organic solvent. The process produces a slurry of ascorbic acid crystals in the organic solvent. Bassford et al., however, do not suggest how to reduce the cost of the starting reactants required in their reaction.

U.S. Pat. No. 2,702,808 to O. Gisvold oxidizes sorbose with nitrogen tetroxide under anhydrous conditions to provide ascorbic acid. D'Addieco's U.S. Pat. No. 2,847,421 provides an intermediate compound with protected alcohol groups which facilitates the synthesis of ascorbic acid from D-sorbitol. D. F. Hinkley et al., in their U.S. Pat. No. 3,721,663, oxidize a lower alkyl sorboside or fructoside to form glycosidic acids which can then give the corresponding ascorbic acid. The initial reactants for this process take the form of either L-sorbose or D-fructose. Consequently, the effort continues to provide the essential nutrient of vitamin C at lower cost.

SUMMARY

Utilizing lactose as the starting material in the synthesis of ascorbic acid provides an inexpensive initial reagent for the production of that vitamin. Deproteinizing whey readily provides a source of lactose. In particular, whey represents an underutilized byproduct in the production of cheese. Thus, it has minimal cost as an initial reagent in the ascorbic acid synthesis.

However, the hydrolysis of lactose produces the two separate sugars, D-galactose and D-glucose in a mixture. Both of these, then, in the mixture must undergo conversion to the ascorbic acid.

The synthesis begins with the hydrolysis of lactose to produce a first mixture of D-galactose and D-glucose. Generally, this reaction proceeds efficiently with the assistance of the enzyme, lactase.

The mixture of D-galactose and D-glucose then undergoes oxidation to produce D-galacturonic acid and D-glucuronic acid in a further mixture. Where the oxidation process may attack the reactants' terminal hydroxyl groups, they may receive the protection of an alkyl or aryl group to form their glycosides. After the oxidation, these additional groups must undergo removal through hydrolysis to leave the desired acids. An oxidizing agent, such as permanganate, can effect the actual oxidation.

The process further proceeds with the reduction of the D-galacturonic and D-glucuronic acids, while mixed together, to provide L-galactonic and L-gulonic acids respectively. Removing the water from a solution containing the latter then forces their conversion to a mixture of their corresponding γ-lactones.

The reverse reaction, which would reconvert the γ-lactones to the acids, proceeds at a relatively slow rate. Accordingly, the γ-lactones may undergo dissolution in water in preparation for the last step. Finally, then, the γ-lactones of L-galactonic and L-gulonic acids, while mixed together, are oxidized to ascorbic acid. Specifically, the oxidation of these acids produces 2-keto-L-galactonic acid and 2-keto-L-gulonic acid. Both then rearrange to ascorbic acid.

The actual oxidation process may conveniently take place in the presence of an enzyme obtainable from animal or vegetable tissue. The enzyme should have the capability of transferring electrons from the γ-lactones to molecular oxygen.

DETAILED DESCRIPTION

Tables A and B show the reactions which, starting with lactose (I), can yield ascorbic acid (IX). The first reaction, labled "(1)" involves the hydrolysis of lactose (I) to produce galactose (II A) and glucose (II B). The compounds and the reactions in Table A represent intermediaries produced from reactions involving, ultimately, galactose (II A). The Roman numerals with the letter "A" indicate the compounds, while the arabic numerals with the letter "A" indicate the reactions, that derive from galactose. Similarly, the compounds and reactions occurring in Table B all bear the designation of "B". Again, Roman numerals indicate compounds and arabic numerals indicate reactions. These latter reactions and compounds involve the glucose moiety produced by the hydrolysis (1) of lactose (I).

1. Hydrolysis of Lactose (I)

The hydrolysis (1) of lactose (I) propitiously proceeds through the use of the enzyme, lactase. U.S. Pat.

No. 2,681,858 to E. G. Stimpson sets forth a procedure for accomplishing this reaction, including the preparation of the lactase. Stimpson operates upon various milk products in order to obtain galactose (II A) and glucose (II B) in the product rather than the combined sugar, lactose (I). Accordingly, he hydrolyzes the lactose while within the milk product.

The synthesis of ascorbic acid, however, only utilizes the lactose component of whey. Where the lactose actually derives from a milk product, the protein contained in it would detract from the final vitamin C. Accordingly, any such protein should generally undergo removal prior to the ascorbic acid synthesis. Alternatively, pure lactose can serve as the beginning reagent.

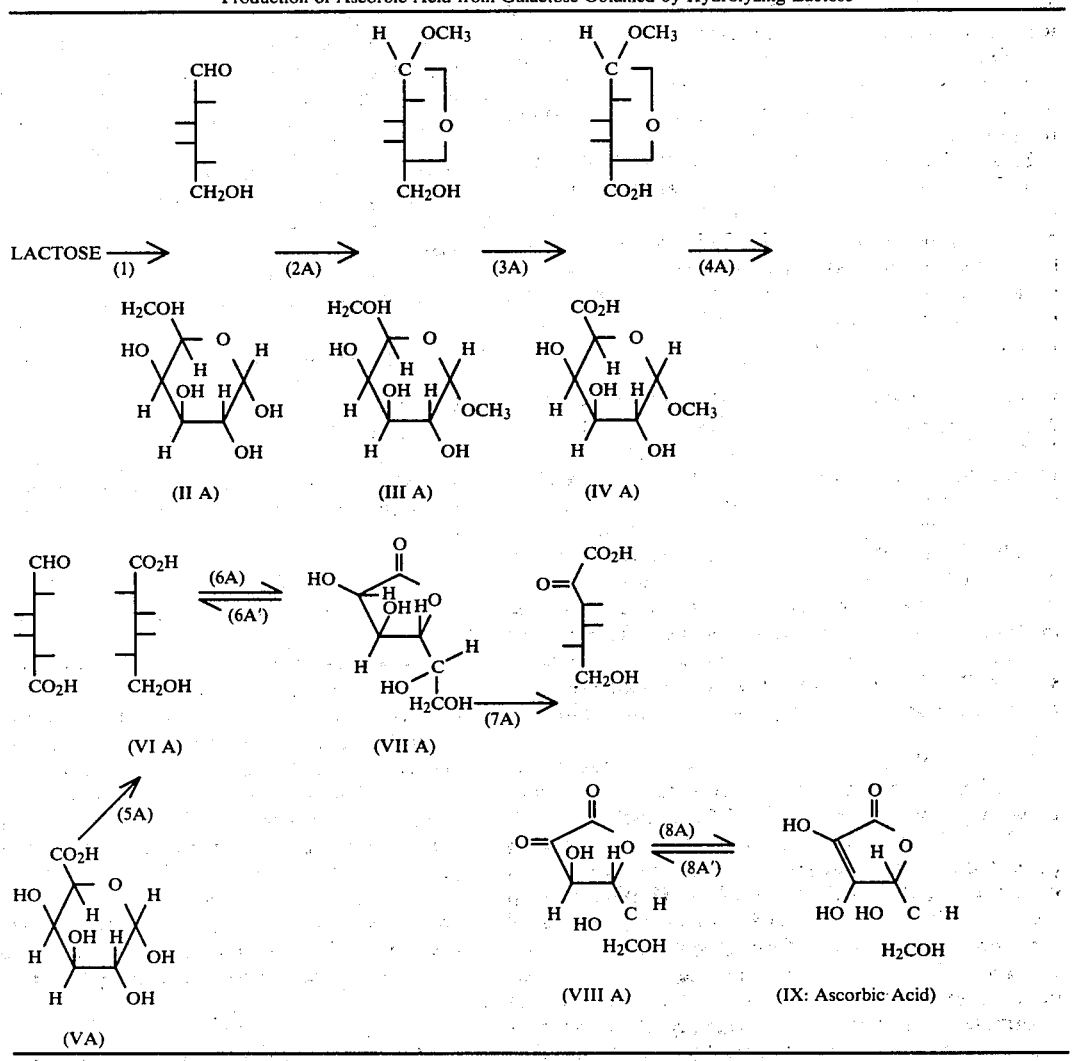

TABLE A
Production of Ascorbic Acid from Galactose Obtained by Hydrolyzing Lactose

TABLE B
Production of Ascorbic Acid from Glucose Obtained by Hydrolyzing Lactose

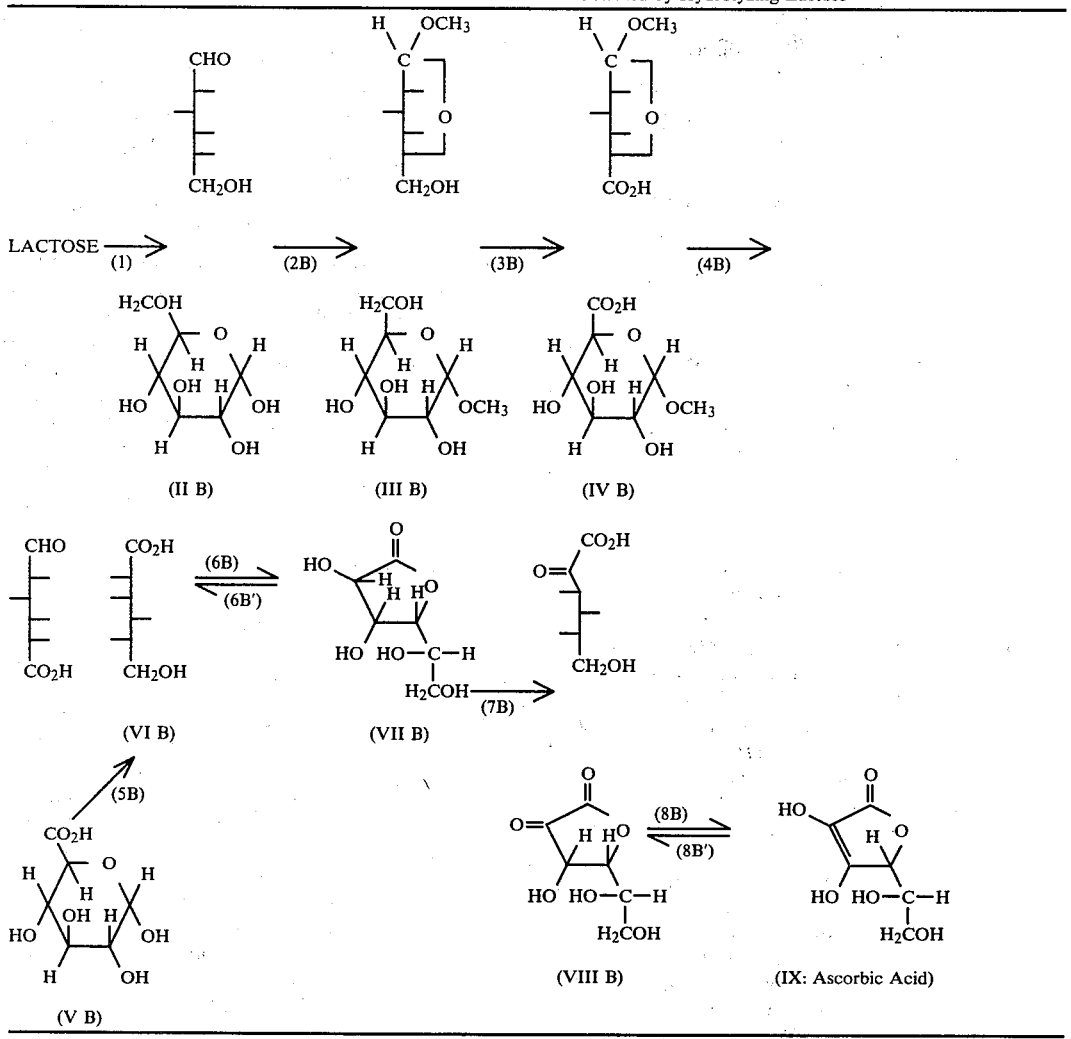

Nonetheless, whey represents a byproduct of the manufacture of cheese. Accordingly, it constitutes an inexpensive source of lactose. To remove the protein, the whey should receive a heat treatment for approximately 20 to 30 minutes at 80° to 90° C. This heating serves to coagulate the protein. Cooling and filtering the solution will remove the coagulated protein.

The deproteinated whey should then generally be evaporated by heating under a partial vacuum until the contents amount to approximately 30 percent by weight in the solution. Alternatively, lactose of, for example, fermentation grade, may be dissolved in warm water to achieve a solids content again of 30 percent by weight.

The lactose solution should have its pH value adjusted to 6.6. The addition, with constant stirring, as necessary, of a 20 percent aqueous sodium hydroxide or 30 percent aqueous hydrochloric acid solution will accomplish this task.

While at a temperature of about 50° to 55° C., the solution of lactose should receive an aqueous slurry of a commercial lactase preparation having maximal available activity. The slurry should contain about one part lactase solids to fifty parts lactose in the solution. The solution with the lactase added remains at the elevated temperature for about 4 to 6 hours. When the concentration of glucose no longer increases, the lactose hydrolysis has reached completion. At this point, almost all of the lactose should have undergone conversion to galactose and glucose.

The use of immobilized lactase appears in an article by A. C. Olson and W. L. Stanley, J. Agr. Food Chem. 21, 440 (1973). A washed and drained sample of phenol-formaldehyde resin of 10 to 40 mesh (sold under the trademark Duolite ® by Diamond Shamrock, Inc.) receives, at room temperature, a solution of commercial, water-soluble lactase from *Aspergillus niger*. The drained resin receives approximately twice its weight of the lactase solution which, in turn, contains approximately 0.5 to 1.0 percent by weight of enzyme.

The resulting suspension, after undergoing gentle stirring for 15 to 30 minutes, receives sufficient glutaraldehyde to form a 1 to 3 percent solution. The stirring then continues for an additional 30 minutes. Subsequently, the mixture temperature is kept at about 5° C. for about 16 hours. The mixture is then placed in a glass column, washed with water, and kept under water at temperatures below 20° C. when not in use. Allowing the enzyme to dry completely destroys its activity even at temperatures as low as 25° C.

To utilize the enzyme, the temperatures of the column increases to 45° C. An acetic acid—sodium acetate buffer (0.05 N in acetate) adjusts the pH of a 3 to 5 percent lactose solution to 4.0. This lactose solution then passes through the column with the immobilized lactase at a rate of approximately 25 ml. per hour.

As a further alternative, lactose in an 18 percent by weight aqueous solution may undergo acid hydrolysis in 0.5 N HCl at 60.1° C. However, Armstrong and Caldwell, Proc. Roy. Soc. (London) 73, 526 (1904), provide results indicating that the acid-catalyzed hydrolysis of lactose proceeds less rapidly than the enzyme-catalyzed hydrolysis. Thus, it would be less economic especially compared to enzyme-catalyzed hydrolysis using immobilized enzyme.

2A and 2B. Preparation of the Methyl Glycosides (III A and III B) of D-galactose (II A) and D-glucose (II B)

U.S. Pat. No. 2,606,186 and J. E. Cadotte et al., J. Am. Chem. Soc. 74, 1501 (1952), provide a method of forming the methyl glycosides of various individual sugars. However, the mixture of glucose and galactose provided above can also submit to this same procedure.

The aqueous solution of these sugars provided from step (1) is evaporated to dryness by using a rotary evaporator in a boiling water bath. A partial vacuum of 30 mm. Hg hastens the process. 540 gm. of the resulting solid mixture of D-galactose (II A) and D-glucose (II B) is added to three l. of methanol in a glass-lined vessel. This vessel should permit the stirring, heating, and refluxing of its contents.

The sugar-methanol solution then receives 150 gm. of sulfonated cross-linked polystyrene in the form of granules or beads (such as Amberlite ® 120, sold by Rohn & Haas Company or Dowex ® 50, sold by The Dow Chemical Company). With continuous stirring, the resulting liquid mixture is heated to the boiling point where it remains for about 24 to 30 hours. Alternatively, the same reaction can take place in a rotating autoclave at a temperature of about 100° to 110° C. for approximately two hours.

Instead of the resin, a soluble, concentrated acid, such as HCl or H$_2$SO$_4$, could be used. Subsequently, the acid would have to undergo neutralization with NaOH which would then form insoluble crystals in the methanol. Filtration would then remove these crystals from the solution.

The solution, which now has the sugar methyl glycosides (III A and III B), is filtered under pressure while hot. The ion-exchange resin, after receiving a washing with methanol, is then ready for further use.

To separate the methyl glycosides, the filtrate cools to about 10° C., where it remains for approximately two hours. This allows most of the product to assume the form of crystals, of which filtration effects the recovery. The filtrate from the latter separation undergoes distillation to concentrate the solution and to recover the methanol. The distillation continues until the volume falls below about 200 ml. A further cooling at about 10° C. for about two hours permits the recovery of additional crystalline material. The crystals constitute an equimolar mixture of the methyl glycosides of D-galactose and D-glucose (III A and III B, respectively).

The methyl glycosides protect the terminal aldehyde group during the subsequent oxidation step (3A and 3B). However, the attachment of other alkyl or aryl groups will accomplish the same result. An alkyl group having from one to four carbon atoms would appear the most propitious choice.

3A and 3B. Oxidation of the Methyl Glycosides (III A and III B) to the Uronic Acids (IV A and IV B).

582 gm. of the crystaline methyl glycosides of glucose and galactose (III A and III B) is dissolved in 2.1 of water at 50° C. The well stirred solution then receives 570 gm. of sodium permanganate at a sufficiently slow rate to preclude its temperature rising above 60° C. After the addition of all of the permanganate, the solution is stirred until a sample of it, after the settling of the sediment, appears colorless. The solution, which becomes alkaline during the oxidation, returns to a neutral pH of 6.5 to 7.5 through the addition of acid and is then filtered to remove the precipitated manganese dioxide.

Alternatively, the oxidation may be performed by employing platinum to catalyze the reaction with an oxygen-bearing gas. The preferred gas, of course, takes the form of air.

4A and 4B. Hydrolysis of the Oxidized Methyl Glycosides (IV A and IV B) to Remove the Methyl Groups.

The filtrate produced during the oxidation step (3A and 3B) above receives sufficient 20 percent aqueous hydrochloric acid to reduce its pH to 1. Heating it at atmospheric pressure effects distillation of the solution. The distillation continues until the distillate no longer contains appreciable amounts of methanol. During this operation, hydrolysis removes the masking methyl group. Also, methanol, with water, distills off from the solution. This aqueous methanol, after redistillation is an efficient column, becomes anhydrous methanol for further use.

After the completion of the distillation, the solution cools to room temperature and then passes through a column packed with sulfonated cross-linked polystyrene resin in the H$^+$ form to remove sodium ions. The effluent carries D-galacturonic acid (V A) and D-glucuronic acid (V B) in an equilibrating mixture with their corresponding lactones.

5A and 5B. Reduction of a Mixture of D-galacturonic acid (V A) and D-glucuronic acid (V B) to a Mixture of L-galactonic acid (VI A) and L-gulonic acid (VI B).

This solution obtained from reaction (4A and 4B) contains an equimolor mixture of D-galacturonic and D-glucuronic acids (V A and V B, respectively) in equilibrium with their corresponding lactones. It receives an Adams type catalyst, which takes the form of 10 percent finely divided platinum carried on charcoal. The amount of the catalyst added equals approximately five percent by weight of the organic acids (V A and V B) undergoing reduction.

Alternately, Raney nickel can perform the catalyzing function. In this instance, two percent by weight of the nickel is added to the solution with the acids.

The suspension with the added catalyst undergoes thorough stirring in a closed vessel fitted for the introduction of gaseous hydrogen. The introduction of the hydrogen occurs at a rate that will maintain the internal pressure at approximately one atmosphere. The addition of the gas continues until the solution takes up no further hydrogen.

The suspension is then filtered and the catalyst washed with water and retained for further use. The solution contains an equimolor mixture of L-galactonic acid (VI A) and L-gulonic acid (VI B) in equilibrium with their corresponding lactones (VII A and VII B, respectively).

6A and 6B. Conversion of L-galactonic acid (VI A) and L-gulonic acid (VI B) to their Corresponding Lactones (VII A and VII B)

The reduction step above (5A and 5B) produces the acids (VI A and VI B) which then equilibrate with their respective lactones (VII A and VII B, respectively) through the reactions (6A and 6B). Of course, part of the lactones (VII A and VII B) will return to the acid form through the reverse reactions (6A' and 6B'). However, the subsequent oxidation step (7A and 7B) can only operate upon the lactone moieties (VII A and VII B). Thus, the free acids (VI A and VI B) must first be converted to the lactone form. To accomplish this, the mixture of the acids (VI A and VI B) produced by the reduction step (5A and 5B), as well as any lactones (VII A and VII B) that may have already appeared, is heated in a rotary vacuum evaporator until no further loss of weight occurs. This indicates that the water content of this solution has reached a minimum. The loss of water forces the equilibrium reaction consisting of (6A) with its reverse reaction (6A') and the corresponding reactions (6B) and (6B') to the right in Tables A and B. The resulting syrup has a mixture of L-galactono-γ-lactone (VII A) and L-gulono-γ-lactone (VII B) with a small amount of the corresponding free acids (VI A and VI B, respectively).

To proceed to the subsequent oxidation reactions (7A and 7B), the lactones thus produced (VII A and VII B) must be redissolved in water. However, the rehydration of the lactones (VII A and VII B) to their free acid forms (VI A and VI B, respectively) through the inverse reactions (6A' and 6B', respectively) proceeds exceedingly slowly. Accordingly, performing the subsequent oxidation reactions (7A and 7B) with dispatch prevents the return of a substantial amount of the lactones to the free acids.

7A and 7B. Oxidation of Lactones (VII A and VII B) to 2-keto-L-galactonic acid (VIII A) and 2-keto-L-gulonic acid (VIII B)

F. A. Isherwood et al, in their British Pat. No. 763,055, have shown that the oxidation of L-galactono-γ-lactone (VII A) and L-gulono-γ-lactone (VII B) can occur outside of a living organism but in the presence of enzymes. These enzymes may be obtained from either animal or vegetable tissue. The enzymes however, should exclude those which can rapidly cause the destruction of ascorbic acid. To effect the oxidation, the enzymes should have the ability to transfer electrons from lactones (VII A and VII B) to molecular oxygen. The patent contains several examples of the obtention and use of the enzymes.

In particular, pea seeds can provide the enzyme for this second oxidation step. To obtain it, 30 gm. of pea seeds are soaked in water at 25° to 30° C. for about 12 to 48 hours. They then undergo crushing in a cooled aqueous solution, preferably at 0° to 4° C. in 40 ml. of an aqueous solution having 0.4 M sucrose, 0.1 M sodium phosphate, a pH of 7.5, and 0.1 percent by weight of magnesium sulfate. Centrifugation then removes starch and cellular debris from the mixture. The turbid supernatant solution contains very fine particles in which the enzymatic activity resides. Its pH value is adjusted to about 7.4 to 7.5.

The equimolor mixture of the γ-lactones of L-galactonic acid (VII A) and L-gulonic acid (VII B), as obtained in step 6A and 6B above, receives the supernate containing the enzyme. This solution then remains at about 36° to 38° C. for about 4 to 6 hours. Adding additional amounts of lactones will permit the production of further product.

The oxidation (7A and 7B) with the enzyme actually produces, initially, 2-keto-L-galactonic acid (VIII A) and 2-keto-L-gulonic acid (VIII B). However, both of these rearrange rapidly according to the reactions (8A and 8B) to give ascorbic acid (IX). The reverse rearrangements (8A' and 8B') occur only to a minimal, if appreciable, extent. Thus, ascorbic acid represents the discernible product from the oxidation reactions (7A and 7B).

The solution containing the ascorbic acid undergoes filtration to clarify it. It should then be evaporated in a rotary evaporator heated in a water bath at 60° C. and at a negative partial pressure of around 30 mm. Hg until the volume reduces to about one fifth of its original. The resulting syrup then cools to room temperature and is thoroughly mixed with an equal volume of acetone. The crystals of ascorbic acid, which have appeared by this point, are recovered by filtration. Cooling the filtrate to 0° C. permits the recovery the additional product.

Accordingly what is claimed is:

1. A method of synthesizing ascorbic acid from lactose comprising:
    A. hydrolizing an aqueous solution of lactose to a first mixture of D-galactose and D-glucose;
    B. converting the D-galactose and D-glucose in said first mixture to a second mixture of the akyl or aryl glycosides of D-galactose and D-glucose;
    C. subsequently oxidizing said second mixture to a third mixture of the alkyl or aryl glycosides of D-galacturonic acid and D-glucuronic acids;
    D. hydrolyzing said glycosides in said third mixture to a fourth mixture of D-galacturonic acid and D-glucoronic acid;
    E. reducing said fourth mixture of D-galacturonic acid and D-glucuronic acid to a fifth mixture of L-galactonic acid and L-gulonic acid;
    F. converting said fifth mixture of L-galactonic acid and L-gulonic acid to a sixth mixture of the γ-lactones of L-galactonic and L-gulonic acids; and
    G. enzymatically oxidizing said γ-lactones of L-galactonic acid and L-gulonic acid, while in said sixth mixture, to ascorbic acid.

2. The method of claim 1 wherein the step of oxidizing said γ-lactones is catalyzed by an enzyme which transfers electrons from sugar lactones to molecular oxygen.

3. The method of claim 2 wherein said alkyl or aryl glycosides in said second mixture are oxidized by adding to an aqueous solution of said alkyl or aryl glycosides permanganate ion while keeping the temperature of said solution of said alkyl or aryl glycosides below about 60° C.

4. The method of claim 3 wherein the alkyl or aryl group of said alkyl or aryl glycosides, respectively, after the step of oxidizing said alkyl or aryl glycosides, is removed by acidifying and distilling an aqueous solution containing the oxidized alkyl or aryl glycosides.

5. The method of claim 4 wherein the alkyl or aryl glycosides of D-glucose and D-galactose are prepared by forming a solution of dry D-glucose and D-galactose with an alcohol and refluxing said solution under acidic conditions.

6. The method of claim 5 wherein said alkyl or aryl group is an alkyl group which has 1 to 4 carbon atoms.

7. The method of claim 6 wherein said alkyl or aryl group is a methyl group.

8. The method of claim 3 wherein the D-glucuronic acid and D-galacturonic acid in said fourth mixture are reduced by passing hydrogen gas into an aqueous solution containing said fourth mixture of acids and a hydrogenating catalyst.

9. The method of claim 8 wherein said hydrogenating catalyst is either 5 percent by weight of said acids of an Adams catalyst or 2 percent by weight of said acids of Raney nickel.

10. The method of claim 8 wherein said lactose is obtained by heating whey to a temperature of about 80° to 90° C. for about 20 to 30 minutes and removing any coagulated protein to produce an aqueous solution of lactose.

11. The method of claim 10 wherein said lactose is hydrolyzed by (1) adding to an aqueous solution containing about 30 percent by weight lactose and having a pH of about 6.6 an aqueous slurry of lactase, said slurry having an amount of lactase equal to about 2 percent by weight of said lactose in said solution to which said slurry is added and (2) maintaining said solution with said lactose and said slurry at a temperature of about 50° to 55° C. for about 4 to 6 hours.

12. The method of claim 10 wherein said enzyme is obtainable from pea seeds.

13. The method of claim 12 wherein:
(1) said enzyme obtainable from pea seeds is prepared by soaking pea seeds in water at about 25° to 35° C. for about 12 to 48 hours, crushing the soaked pea seeds in a cooled aqueous solution at about 0.4 M sucrose, 0.1 M phosphate ion, pH 7.5, and 0.1 percent by weight magnesium sulfate and removing starch and solid cellular debris from the solution with said crushed pea seeds to give a turbid solution; and
(2) said γ-lactones of L-galactonic acid and L-gulonic acid are oxidized to L-ascorbic acid by adding to said turbid mixture with a pH of about 7.4 to 7.5 said sixth mixture with said lactones and maintaining said turbid solution with said sixth mixture at about 36° to 38° C. for about 4 to 6 hours.

14. The method of claim 13 wherein the step of converting said fifth mixture of L-galactonic and L-gulonic acids to said lactones is performed by the removal of water from an aqueous solution containing said fifth mixture of acids and, after the removal of water, the solution with said sixth mixture is redissolved in further water prior to oxidizing said lactones to ascorbic acid.

15. The method of claim 14 wherein said soaked pea seeds are crushed in an aqueous solution at about 0° to 4° C.

* * * * *